United States Patent [19]
Keister et al.

[11] Patent Number: 4,964,877
[45] Date of Patent: Oct. 23, 1990

[54] NON-AQUEOUS LITHIUM BATTERY

[75] Inventors: Pamela P. Keister, Clarence; Ralph T. Mead, Kenmore; Barry C. Muffoletto, Alden; Esther S. Takeuchi, Snyder; Steven J. Ebel, Tonawanda; Michael A. Zelinsky, Lancaster; John M. Greenwood, Williamsville, all of N.Y.

[73] Assignee: Wilson Greatbatch Ltd., Clarence, N.Y.

[21] Appl. No.: 323,281

[22] Filed: Mar. 14, 1989

Related U.S. Application Data

[62] Division of Ser. No. 818,879, Jan. 14, 1986, Pat. No. 4,830,940.

[51] Int. Cl.$^5$ ............................................. H01M 6/00
[52] U.S. Cl. .................................. 29/623.1; 29/623.2; 429/137
[58] Field of Search ..................... 29/623.1, 623.3; 429/137, 94

[56] References Cited

U.S. PATENT DOCUMENTS

| | | | |
|---|---|---|---|
| 4,019,251 | 4/1927 | McCole | 29/623.3 X |
| 4,051,304 | 9/1977 | Snook | 429/94 |
| 4,594,299 | 6/1986 | Cook et al. | 29/623.3 X |
| 4,761,352 | 8/1988 | Bakos et al. | 429/94 |
| 4,824,744 | 4/1989 | Kuo et al. | 29/623.3 X |

FOREIGN PATENT DOCUMENTS 2088119  6/1982  United Kingdom .............. 429/128

Primary Examiner—Stephen J. Kalafut
Attorney, Agent, or Firm—Edwin T. Bean, Jr.; Martin G. Linihan; John C. Thompson

[57] ABSTRACT

A solid cathode liquid organic electrolyte lithium cell for delivering high current pulses comprising a casing, a cathode structure in the casing comprising a plurality of plates in spaced apart relation, a lithium anode comprising a plurality of anode sections interposed between the cathode plates, a non-aqueous liquid organic electrolyte comprising the combination of a lithium salt and an organic solvent in the casing operatively contacting the anode and the cathode an electrical connection provided to the anode and an electrical connection provided to the cathode. In accordance with one aspect of the invention the cathode includes as active material $Ag_xV_2O_y$ where x is in the range from about 0.5 to about 2.0 and y is in the range from about 4.5 to about 6.0 which advantageously has high volumetric capacity and high rate capability with the result that the cell of the present invention delivers high capacity, shows good current pulsing behavior at various levels of discharge, and has a sloping discharge cause enabling end of life to be predicted.

9 Claims, 8 Drawing Sheets

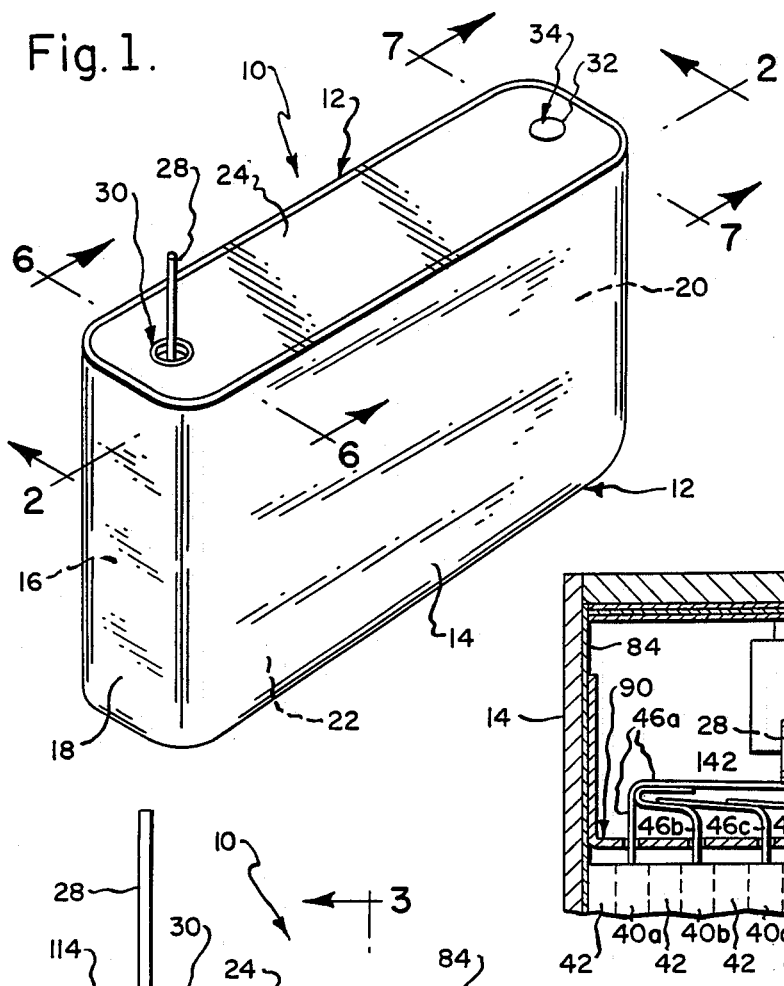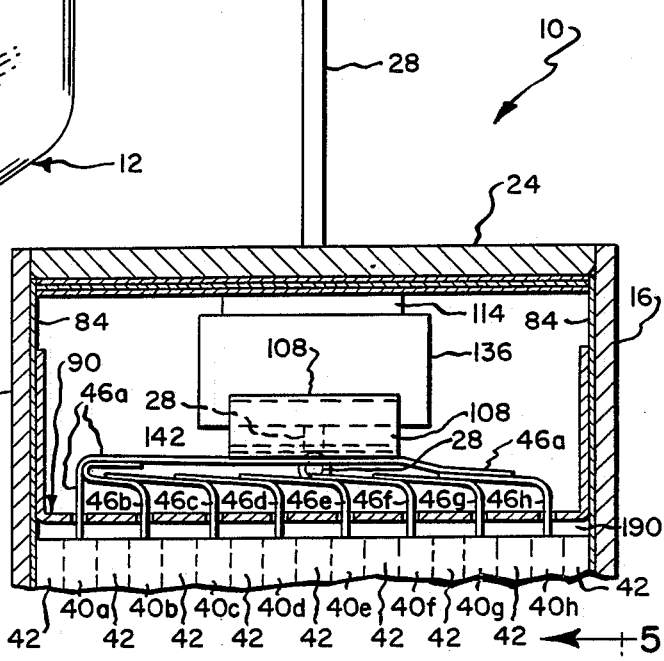

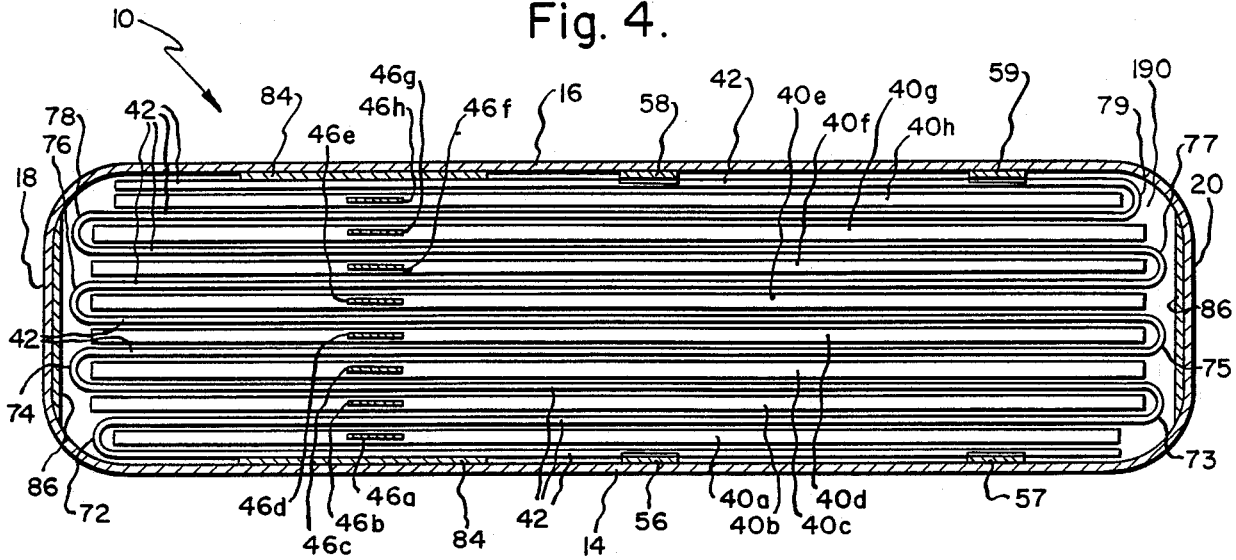
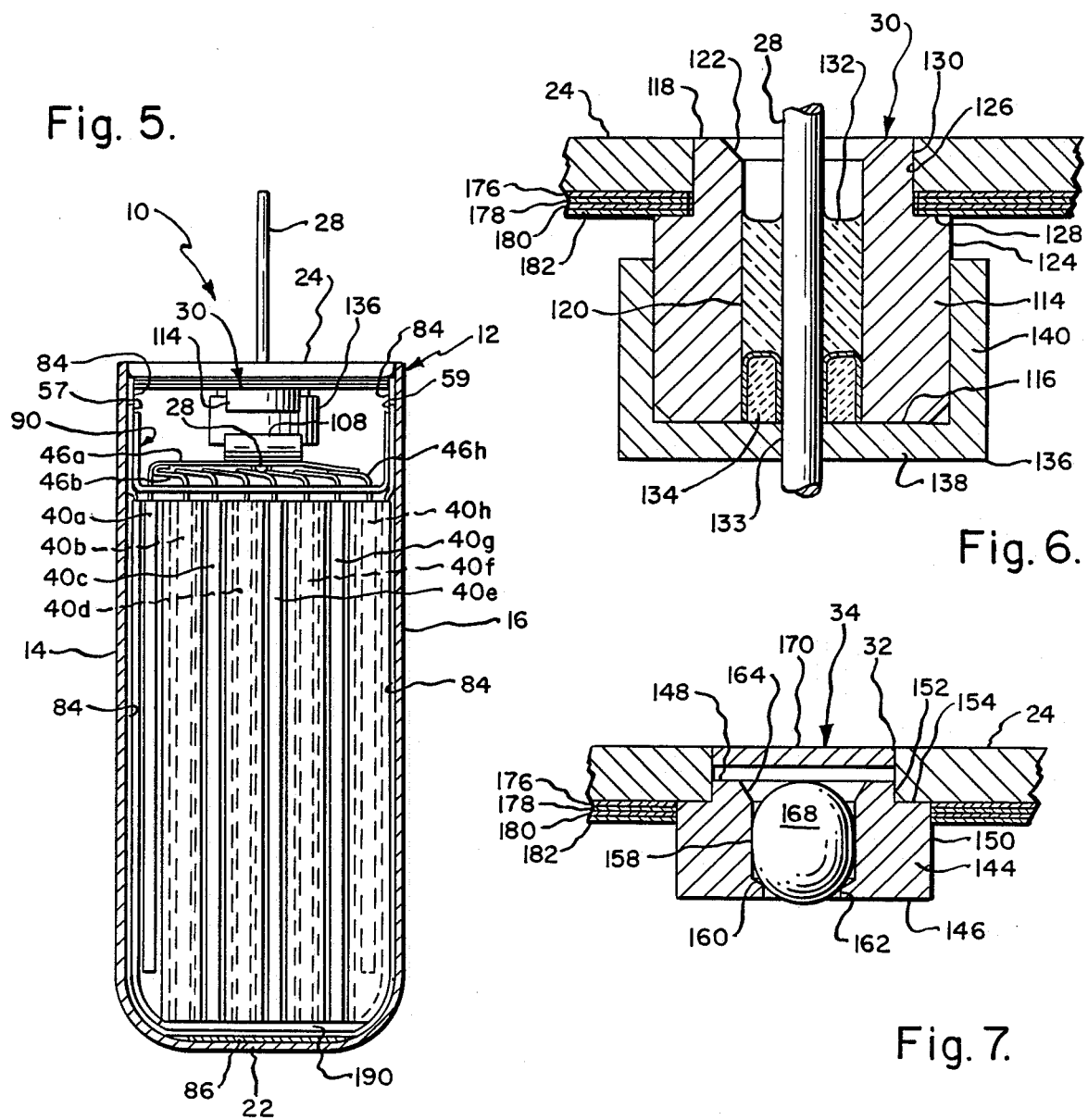

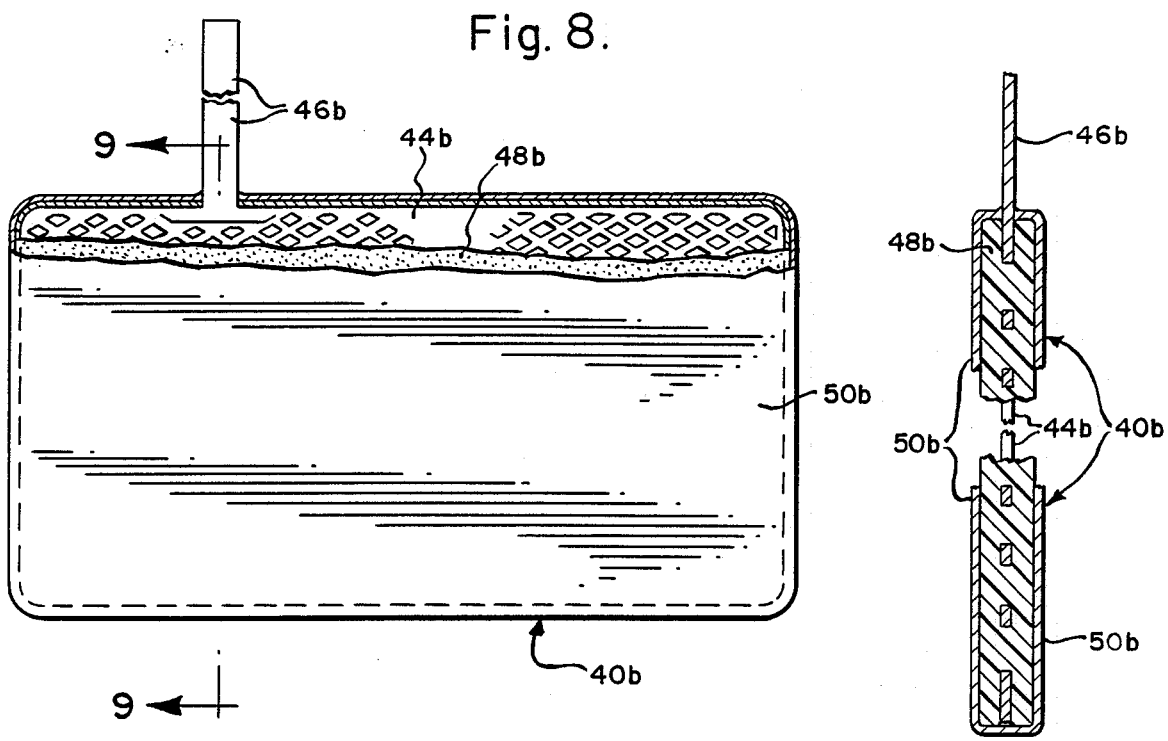
Fig. 8.
Fig. 9.
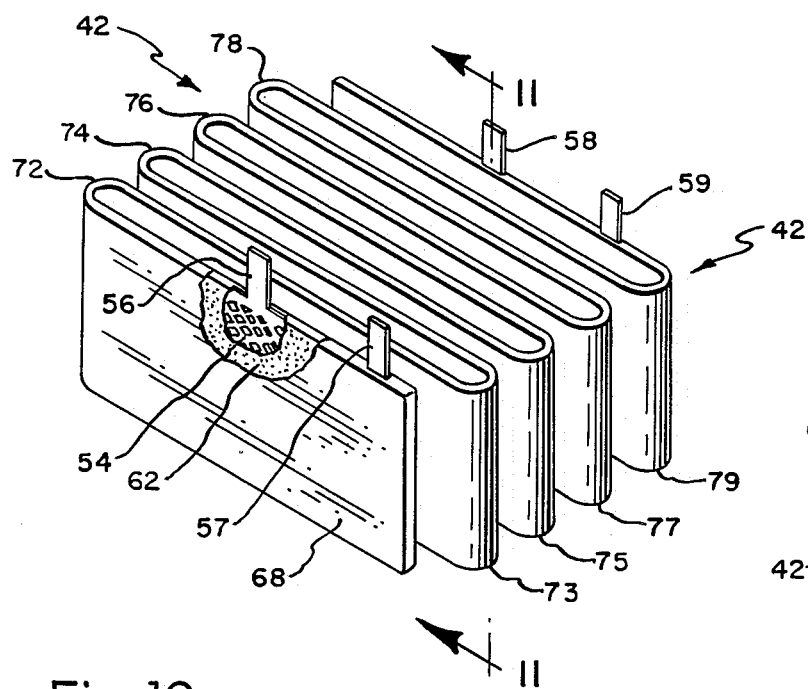
Fig. 10.
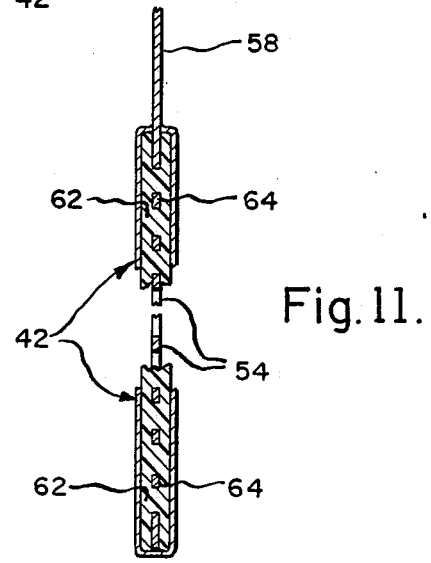
Fig. 11.

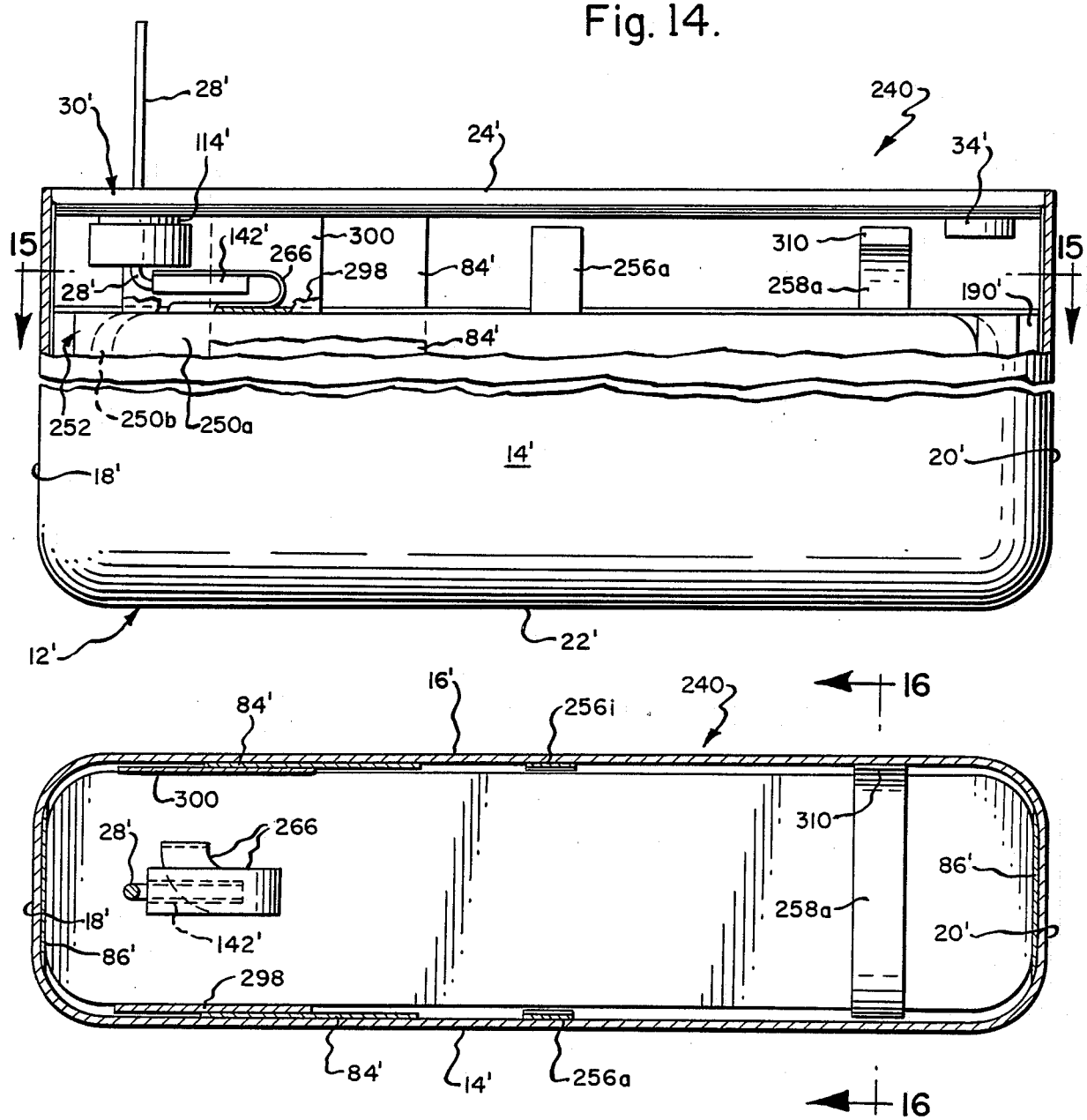

Fig. 20.
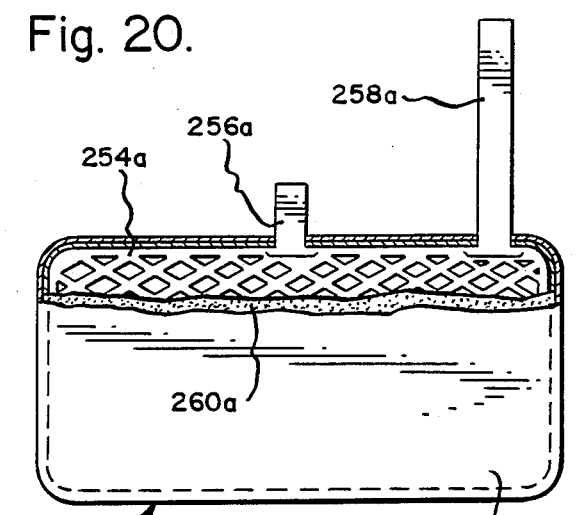
Fig. 21.
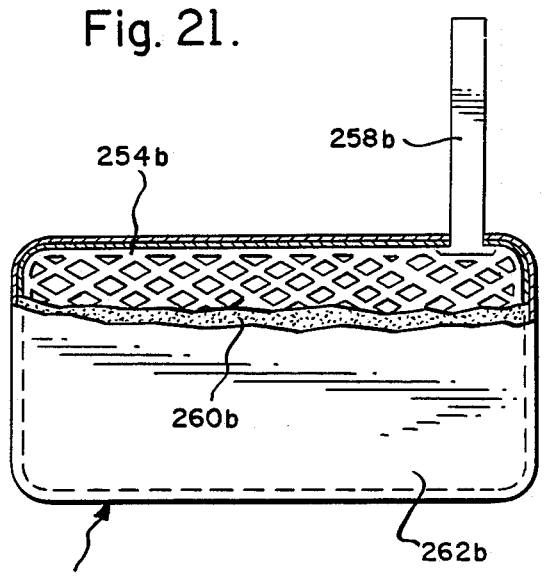
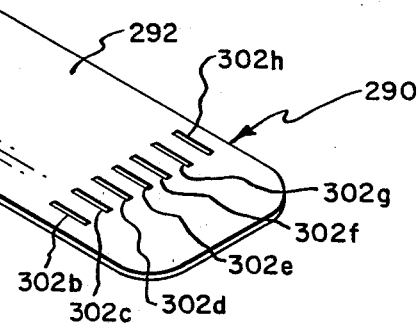
Fig. 22.
OPEN CIRCUIT AND VOLTAGE UNDER PULSE VS. CAPACITY
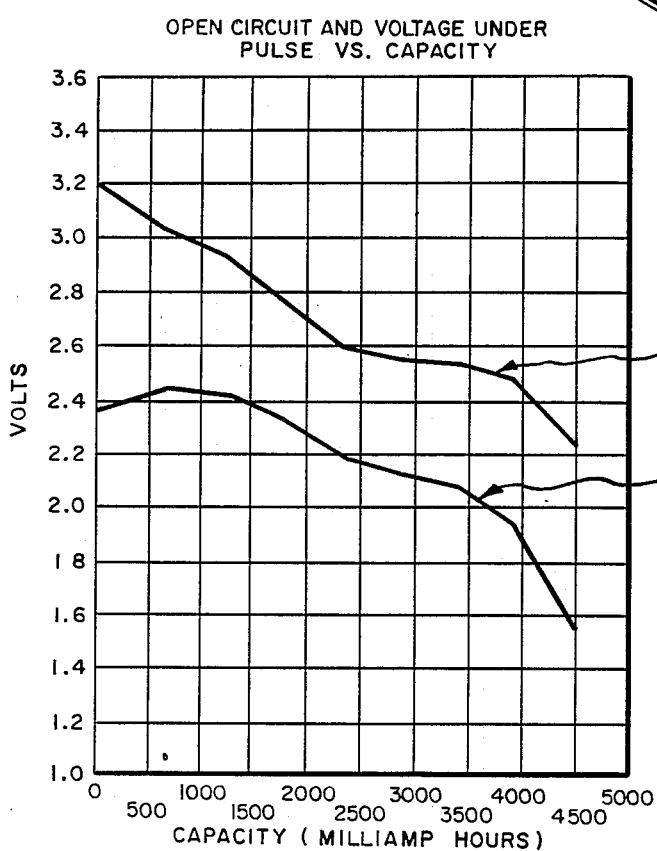
Fig. 28.

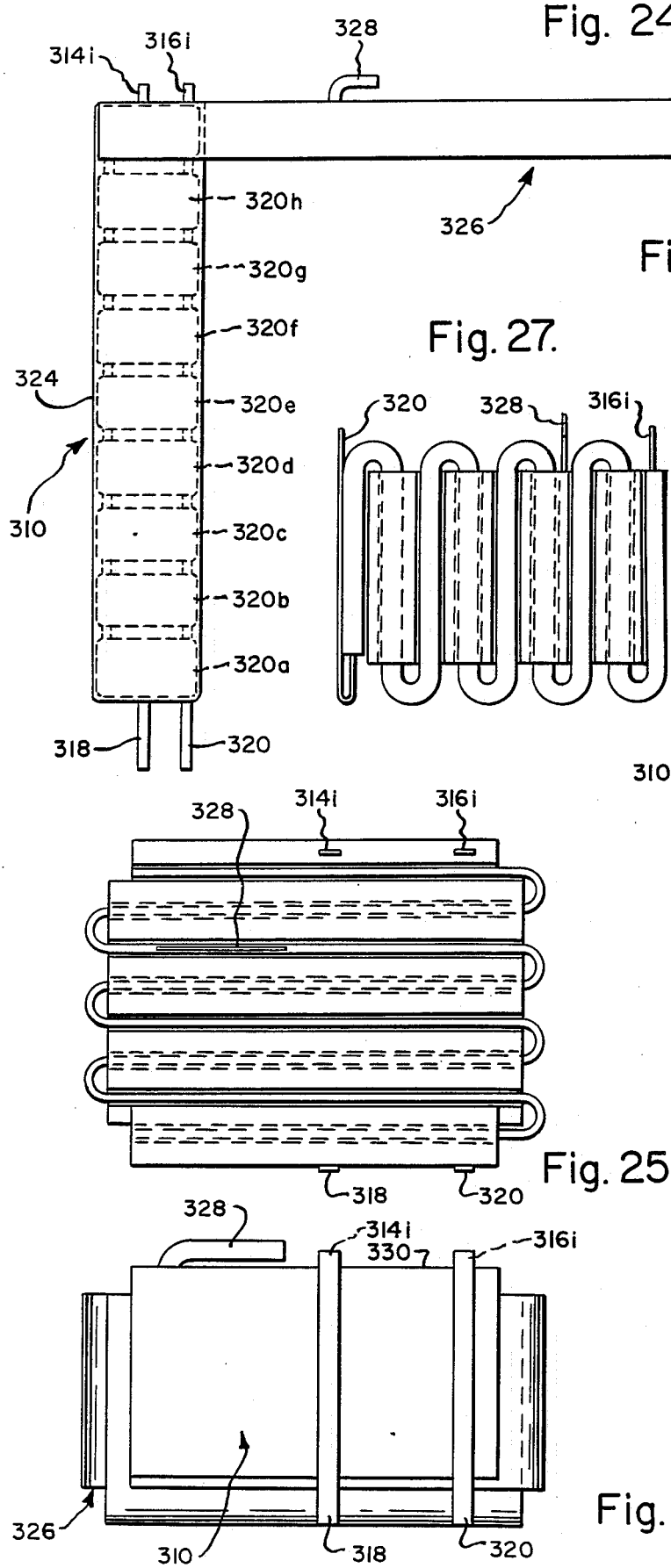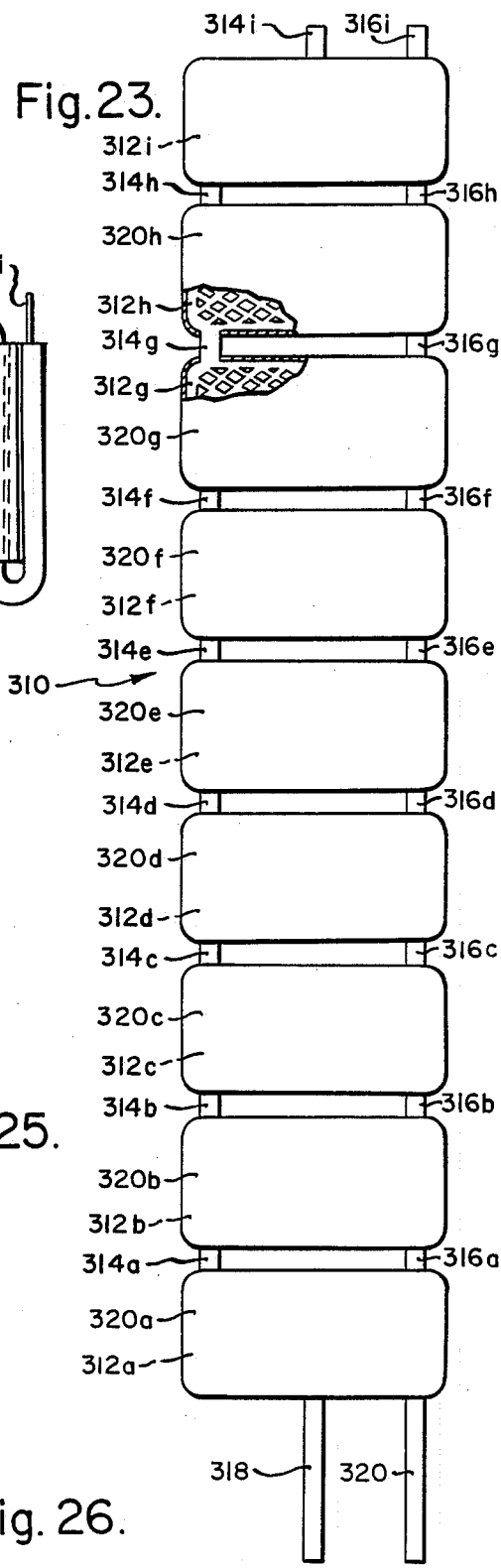

NON-AQUEOUS LITHIUM BATTERY

This is a divisional of co-pending application Ser. No. 06/818,879 filed on Jan. 14, 1986 now U.S. Pat. No. 4,830,940.

BACKGROUND OF THE INVENTION

This invention relates to the art of lithium batteries, and more particularly to a new and improved solid cathode, liquid organic electrolyte lithium battery for delivering high current pulses.

One area of use of the present invention is with an implantable cardiac defibrillator, although the principles of the present invention can be variously applied. Recent advances in the implantable cardiac device industry have led to the development of implantable cardioverter/defibrillators. The purpose of the implantable defibrillator is to prevent sudden death from lethal arrythmia. In operation, the defibrillator device continuously monitors the heart rate of the patient, is able to recognize ventricular fibrillation, and subsequently delivers high energy shocks to defibrillate the heart.

Concurrently, there developed a need for batteries to power this type of device. In particular, the ability of an implantable battery to deliver a current pulse and rapidly recover its open circuit voltage has become an important performance characteristic. Defibrillatiors are expected to function alone or in conjunction with a pacemaker, thus demanding high capacity, low self-discharge, and good pulsing behavior of a power source at all levels.

SUMMARY OF THE INVENTION

It is, therefore, a primary object of this invention to provide a new and improved solid cathode, liquid organic electrolyte lithium battery for delivering high current pulses.

It is a further object of this invention to provide such a battery having the ability to deliver a current pulse and rapidly recover its open circuit voltage.

It is a further object of this invention to provide such a battery having high capacity, low self-discharge, and good pulsing behavior at all levels.

It is a further object of this invention to provide such a battery having the requisite safety in operation and proper size and configuration suitable for implantation.

It is a further object of this invention to provide such a battery wherein the cell chemistry includes a reliable indication of the depth of discharge or approaching end-of-life during operation.

It is a further object of this invention to provide such a cell which is economical to manufacture and efficient and effective in operation.

The present invention provides a solid cathode liquid organic electrolyte lithium cell for delivering high current pulses comprising a casing, cathode means in the casing comprising a plurality of plates in spaced apart relation, lithium anode means comprising a plurality of anode sections interposed between the cathode plates, a non-aqueous liquid organic electrolyte comprising the combination of a lithium salt and an organic solvent in the casing operatively contacting the anode means and the cathode means, means for providing electrical connection to the anode means and means for providing electrical connection to the cathode means. In accordance with one aspect of the invention the cathode means includes as active material $Ag_xV_2O_y$ where x is in the range from about 0.5 to about 2.0 and y is in the range from about 4.5 to about 6.0 which advantageously has high volumetric capacity and high rate capability with the result that the cell of the present invention delivers high capacity, shows good current pulsing behavior at various levels of discharge, and has a sloping discharge curve enabling end of life to be predicted. In accordance with another aspect of the present invention, the anode means comprises a continuous elongated lithium element enclosed within a separator and folded into a plurality of sections interposed between the cathode plates, each of which individually is enclosed within separator material thereby enhancing the reliability of the cell. The cathode plates can be formed by an entirely dry pressing procedure thereby enhancing the shelf life of the resulting plates or, alternatively the procedure can include dropwise addition of liquid electrolyte to the cathode mixture prior to pressing to enhance the performance and rate capability of the cell. The cell of the present invention finds advantageous use as a power source for an implantable cardiac defibrillator.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 1 is a perspective view of a solid cathode liquid organic electrolyte lithium battery for delivering high current pulses according to the present invention;

FIG. 2 is a longitudinal sectional view taken about on line 2—2 in FIG. 1;

FIG. 3 is a fragmentary sectional view taken about on line 3—3 in FIG. 2;

FIG. 4 is a sectional view taken about on line 4—4 in FIG. 2;

FIG. 5 is a sectional view taken about on line 5—5 in FIG. 2;

FIG. 6 is a fragmentary sectional view taken about on line 6—6 in FIG. 1;

FIG. 7 is a fragmentary sectional view taken about on line 7—7 in FIG. 1;

FIG. 8 is an elevational view, with parts removed, of one of the cathode plates in the battery of FIG. 1;

FIG. 9 is a transverse sectional view taken about on line 9—9 in FIG. 8;

FIG. 10 is a perspective view, with parts removed, of the anode in the battery of FIG. 1;

FIG. 11 is a transverse sectional view taken about on line 11—11 in FIG. 10;

FIG. 14 is a fragmentary side elevational view with parts removed and partly in section of a battery according to another embodiment of the present invention;

FIG. 15 is a sectional view taken about on line 15—15 in FIG. 14;

FIG. 16 is a fragmentary sectional view taken about on line 16—16 in FIG. 15;

FIG. 20 is an elevational view with parts removed of one of the outer cathode plates in the battery of FIG. 14;

FIG. 21 is an elevational view with parts removed of one of the inner cathode plates in the battery of FIG. 14;

FIG. 22 is a perspective view of a component of the battery of FIG. 14;

FIG. 23 is an enlarged elevational view of an alternative form of cathode useable in the battery of the present invention;

FIG. 24 is an elevational view of the finished cathode of FIG. 23 and an anode in positional relationship prior to folding into a cell stack assembly;

FIG. 25 is a top plan view of the resulting cell stack assembly formed from the cathode and anode shown in FIG. 24;

FIG. 26 is a side elevational view of the cell stack assembly of FIG. 25; and

FIG. 27 is an end elevational view thereof;

FIG. 28 is a graph of open circuit and voltage under pulse vs. capacity for an illustrative battery of FIGS. 1–12.

DETAILED DESCRIPTION OF THE ILLUSTRATED EMBODIMENTS

Figure 12:
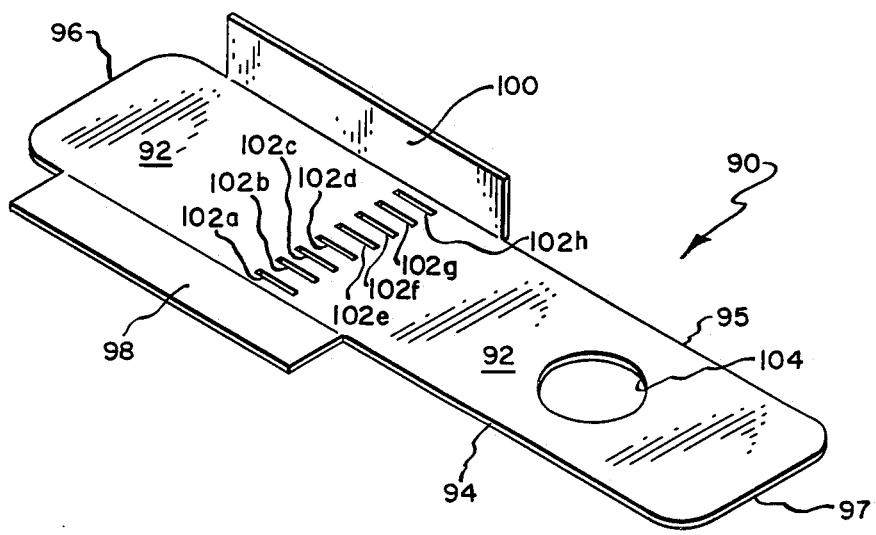
FIG. 12 is a perspective view of a component of the battery of FIG. 1.

The requirements for a suitable power source for an implantable cardiac defibrillator include the following. The cell must have a high rate capability in that it must be able to deliver pulses having an amplitude from about one ampere to about three amperes, having energy from about 25 to about 50 joules and having a duration of about ten seconds from a microampere background current. The cell must be able to deliver a plurality of such pulses in succession, for example five, with the pulses being separated by about ten to fifteen seconds rest on open circuit or a microamp background. The nature of the battery must be such that the voltage recovers rapidly, i.e. within about ten seconds, to near the battery open circuit voltage or to the background voltage from the pulse load voltage. The cell must be hermetically sealed and must exhibit safety characteristics consistent with implantable grade standards thereby presenting no hazard under normal operating conditions. The cell chemistry must have inherently low self-discharge to allow years of service, and the cell must have sufficient capacity to provide three to five years operation of the implanted defibrillator. The cell must be a high energy density system to allow a small size for implantation, and the cell must be manufactured in a shape suitable for implantable devices. The nature of the cell chemistry must include a reliable indication of depth of discharge or approaching end-of-life during operation.

Referring now to the drawings, FIG. 1 shows a battery 10 according to the present invention for delivering high current pulses and particularly suited as a power source for an implantable cardiac defibrillator. Battery 10 includes a hollow casing 12 having spaced apart side walls 14,16, spaced apart end walls 18,20 and a bottom wall 22. Casing 12 is closed at the top by a lid 24 welded in place in a known manner. Casing 12 is of metal such as stainless steel, and being electrically conductive provides one terminal or contact for making electrical connection between the battery and its load in a manner which will be described. Lid 24 also is of stainless steel. The other electrical terminal or contact is provided by a conductor or pin 28 extending from within battery 10 through casing 12, in particular through lid 24. Pin 28 is insulated electrically from the metal lid 24 by an insulator and seal structure 30 which will be described in detail presently. A fill opening 32 in lid 28 is closed by a cap 34 in a manner which will be described.

The battery 10 of the present invention further includes cathode means 40 in casing 12 comprising a plurality of components or plates in spaced apart relation and lithium anode means 42 comprising a plurality of anode sections interposed between the cathode plates. Referring first in detail to cathode means 40, in the battery 10 of the present illustration there are eight cathode plates 40a, 40b, 40c, 40d, 40e, 40f, 40g, and 40h. The cathode plates 40a–40h are arranged in casing 12 in spaced-apart, stacked relation and disposed substantially parallel to each other and to the sidewalls 14,16 of casing 12. The cathode plates 40 are generally rectangular in overall shape and of a size extending along substantially the entire dimension of casing 12 between ends 18, 20 and extending along a major portion of the distance between bottom 22 and lid 24. As shown in FIGS. 2 and 4 the outermost cathode plates 40a and 40h in the stack are slightly shorter in length and in width than the remainder of the cathode plates 40b–40g to accommodate the curved ends 18 and 20 and the curved bottom 22 of casing 12.

In accordance with the present invention, the cathode means 40 contains as cathode active material silver vanadium oxide, $Ag_xV_2O_y$ where x is in the range from about 0.5 to about 2.0, preferably from about 0.95 to about 1.1 and y is in the range from about 4.5 to about 6.0, preferably from about 5.0 to about 6.0. The silver vanadium oxide active cathode material in the cell of the present invention advantageously delivers high capacity, has a sloping discharge curve thereby enabling end of life of the battery to be predicted and shows good current pulsing behavior at various levels of discharge as will be described.

FIGS. 8 and 9 show in further detail one of the cathode components or plates, for example cathode component 40b. Cathode 40b comprises a cathode conductor including a body portion 44b and a lead portion 46b. The conductor portion 44b is in the form of a thin sheet of metal screen, for example titanium or stainless steel, and lead portion 46b is in the form of a solid thin tab extending from one side of screen 44b. Cathode 40b further comprises a body 48b of cathode mixture including cathode active material and binder. The cathode active material is silver vanadium oxide as previously described, and can include a binder such as Teflon and can include conductors such as graphite powder and acetylene black powder. In addition, the cathode mixture can contain an additive such as lithium salts, solid lithium ion conducting electrolyte and surfactant. The manner in which the cathode mixture is prepared will be described further on in the specification. After preparation of the mixture it is pressed onto cathode conductor body portion 44b in a manner which will be described to form a pellet. Following that the pellet is enclosed in an envelope 50b of separator material, for example, polypropylene or polyethylene, in a manner which will be described. All of the other cathode components or plates 40a and 40c–40h are identical in construction to cathode 40b. Cathodes 40a and 40b are different in dimension only, as previously described.

Referring now in detail to the anode means 42, in the battery of the present illustration anode means 42 comprises a continuous elongated element or structure of alkali metal, preferably lithium or lithium alloy, enclosed within separator material and folded into a plurality of sections which are interposed between the cathode plates 40a–40h. As shown for example, in FIG. 4, anode means 42 is folded in a manner such that the sections thereof extend along both opposite sides of each of the cathode plates 40a–40h. Thus, the two sections of anode means 42 at the opposite ends thereof are located between the outer faces of cathode plates 40a and 40h and the corresponding inner surfaces of casing sidewalls 14 and 16. Referring now in detail to FIGS. 10 and 11, anode means 42 comprises an elongated continuous ribbon-like anode conductor element 54 in the form of thin metal screen, for example nickel. Conductor 54 includes at least one terminal or contact tab extending therefrom, and in the battery shown there are four tabs 56, 57, 58 and 59 extending out from the same side edge of conductor 54 and arranged in two pairs, each pair being located in proximity to a corresponding one of the ends of conductor 54 and the tabs of each pair being spaced apart a distance less than the length of the corresponding casing sidewall 14,16. Anode means 42 further comprises a pair of elongated ribbon-like lithium elements 62 and 64 pressed together against opposite sides of conductor element 54 to form an anode structure. The lithium elements 62, 64 are substantially equal in width and length to conductor element 54. The resulting anode structure is a sandwich-like construction with conductor 54 between the lithium elements 62,64. Anode means 42 further comprises separator material 68 encapsulating the anode structure. In particular, the anode structure comprising conductor 54 and lithium plates 62,64 is enclosed or wrapped in an evelope of separator material, for example polypropylene or polyethylene, in a manner which will be described.

The resulting anode structure 42 is folded at spaced intervals along the length thereof to form a serpentine-like structure as shown in FIG. 10 to receive between the folds thereof the plurality of cathode plates. In particular, the anode means 42 is folded at the intervals 72,73,74,75,76,77,78 and 79 along the length thereof. Cothode plate 40a is received between the folds or leaves in anode 42 defined about interval 72 as shown in FIG. 4. Cathode plate 40b is received between the folds defined about interval 73. Similarly, the remaining cathode plates 40c–40h are received between the folds defined about the intervals 74–79, respectively.

The folded anode structure 42 with cathode plates 40a–40h received therein comprises a cell stack subassembly which is received in casing 12. The opposite end portions of anode 42 which are defined between each of the folds 72 and 79 and the corresponding end edges of the anode are located being adjacent the inner surfaces of casing sidewalls 14, 16. The cell stack occupies a major portion of the interior volume of casing 12 between sidewalls 14, 16, between end walls 18, 20 and extending from bottom wall 22 to a location spaced a distance from the casing lid 24 defining an open region therebetween. A first cell stack insulator 84 in the form of a thin elongated band or strip extends along casing sidewalls 14, 16 and bottom wall 22 as shown in FIGS. 2–5 and is located between the inner wall surfaces of the casing and the outer surfaces of the cell stack, particularly the outer surfaces of the afore-mentioned anode portions. A second cell stack insulator 86 similar to insulator 84 extends along casing end walls 18, 20 and bottom wall 22 as shown in FIGS. 2–5 and is between the inner wall surfaces of the casing and the outer end and bottom surfaces of the cell stack. Insulators 84, 86 are provied to prevent internal electrical short circuits. By way of example, both insulators 84 and 86 can be of Halar or Tefzel material. As an alternative, a single container or bag of insulating material holding the cell stack assembly can be employed.

A cell stack insulating cover 90 is located in casing 12 adjacent the upper surface of the cell stack and in spaced relation to lid 24 as viewed in FIGS. 2, 3 and 5. Cover 90, shown in further detail in FIG. 12, has a planar body portion 92 including parallel side edges 94,95, parallel end edges 96,97 and curved or rounded corners so as to conform closely to the configuration defined by the inner surfaces of the casing sidewalls 14,16 and end walls 18,20. Cover 90 is provided with a pair of flanges or tabs 98 and 100 extending from side edges 94 and 95 and disposed at about right angles to body 92. Tabs 98,100 are used to insulate the cathode leads from the inner surface of casing sidewalls 14,16 Body 92 is provided with a plurality of spaced-apart, longitudinally disposed slots 102a–102h which are arranged in a row extending transversely across body 92. Slots 102a–102h are of a size, configuration and location to receive tabs 46a–46h, respectively extending from cathode pellets 40a–40h, respectively. Thus, the cathode leads or tabs 46a–46h extend from cathode plates or pellets 40a–40h in the stack below cover 90 and they extend through the slots 102–102h into the open region between cover 90 and lid 24. Cover body 92 is provided with an opening 104 near the opposite end as viewed in FIG. 12 for a purpose to be described.

Each of the cathode leads 46c–46h is bent or formed into approximately a right angle as shown in FIG. 3 with the legs thereof extending in the same direction and with the lower surface of one leg contacting and secured such as by welding to the upper surface of the neighoring leg. Lead 46b is bent into a formation including a right angle portion like the other leads and then the outer end is formed into a return bend. Lead 46a is of considerably greater length than the other leads and is bent into a right angle extending in the opposite direction and overlying the remaining tabs 46b–46h as shown in FIG. 3. Lead 46a is connected to lead 46b as shown. The remaining end portion of lead 46a extends transversely and is welded to lead 46h. An intermediate lead 108 in the form of a ribbon or strip is fixed at one end to lead 46a and extends longitudinally relative to body 90 and casing 12 and is provided for connection to terminal pin 28a through the insulator and seal structure 30 which now will be described.

As shown in FIG. 6, the insulator and seal structure 30 comprises a header or ferrule element 114 generally in the form of a cylindrical bushing of metal such as stainless steel. Header 114 has opposite axial end faces 116 and 118 and a longitudinal through bore or passage 120 of constant diameter. End face 116 and bore 120 meet in an annular surface 122 generally in the form of a countersunk surface. The outer surface of header 114 includes a first diameter portion 124 extending from end face 116 along the major portion of the axial length of ferrule 114, a second smaller diameter portion 126 extending inwardly from end face 118 along a smaller portion of the length, the portions 124,126 meeting in an annular surface 128 defining a shoulder. The smaller diameter section 126 is fitted in an opening 130 in lid 24 with the end face 118 being flush with the outer surface of lid 24 and ferrule 114 is secured in place by welding. The conductor or pin 28 is held and sealed within bore 120 by a body 132 of glass. The glass seal 132 occupies a major portion of the length of bore 120. There is also provided a body 134 of elastomer material between end face 116 and glass seal 132. Preferably, pin 28 and seal 132 are of corrosion resistant pin-glass combinations such as molybdenum and Ta23 glass.

The insulator and seal structure 30 is completed by an insulator element 136 in the form of a cup having a base 138 and annular rim portion 140. By way of example, insulator 136 can be of Halar or Tefzel material. Base 138 is provided with a central opening 133 through which conductor 28 extends. The inner diameter of rim portion 140 is substantially equal to the diameter of header portion 124 so that insulator 136 is received on header 114 in a snug tight fitting relationship. When insulator 136 is in place, the inner surface of base 138 contacts the header end surface 116, and rim 140 terminates a short distance from the shoulder 128. Thus, as shown in FIG. 6, conductor pin 28 extends through and is held and sealed in the insulator and seal structure 30, the portion of pin 28 within casing 12 is formed into a right angle bend as shown in FIGS. 2 and 3 and is snugly fitted into one end of a coupling sleeve 142 which, in turn, is secured such as by welding to the intermediate lead 108.

Lid 24 is provided with a fill opening 32 which is closed by a cap structure 34 shown in further detail in FIG. 7. The cap or closure 34 includes a ferrule element 144 having a pair of opposite end faces 146, 148. An outer surface extends between the end faces and includes a first diameter portion 150 extending from the end face 146 along substantially the entire length and a second smaller diameter portion 152 extending from end face 148, the portions 150,152 being joined by an annular surface 154 defining a shoulder. The central or longitudinal passage or opening in ferrule 144 includes a section 158 of constant diameter extending along substantially the entire axial length. Near end face 146, section 158 terminates in an annular seating surface 160, which, in turn, meets a smaller diameter section 162 which extends in from end face 146. An annular countersunk surface 164 extends in from the other end face 148 and meets section 158. The cap structure further includes a first plug in the form of a ball or sphere element 168 having an outer diameter substantially equal to the diameter of section 158. Plug 168 is received in section 158 and rests on the seating surface 160. The ferrule 144 is fitted in the lid opening 32 with section 152 extending therein and surface 154 contacting the inner surface of lid 24. Ferrule 144 is fixed in place by welding. The cap structure 34 is completed by a second plug in the form of a cap or disc 170 fitted in opening 32 and secured therein by welding. By way of example, ferrule 144, plug 168 and cap 170 all can be of stainless steel.

The subassembly including lid 24 insulator and seal structure 30 and the cap structure 34 is completed by the provision of a plurality of shield elements or strips adjacent the inner surface of lid 24. Each of the elements is in the form of a thin plate-like strip elongated rectangular and of a size and configuration to cover the surface of lid 24 and provided with openings to accommodate the steel structure 30 and cap structure 34. The first shield element 176 is located adjacent and in contact with the inner surface of lid 24. A second shield element 178 is adjacent and in contact with shield 176. A third shield 180 is adjacent and in contact with shield 178. The shields 176, 178 and 180 function as heat shields to protect the internal components of battery 10 including the electrolyte within casing 12 from heat during welding of lid 24 to casing 12 and the cap structure 34 to lid 24. By way of example, in an illustrative battery, shields 176 and 178 are of stainless steel and shield 180 is of mica. A fourth shield 182 is located adjacent and in contact with shield 180. It serves as an insulator between the lid assembly and the remainder of the cell, and by way of example can be of Halar or Tefzel material. Each shield element is provided with a circular opening near one end to accommodate the insulator and shield structure 30 and with a notch-like opening extending in from the opposite end and terminating in a semi-circular inner end to accommodate the cap structure 34.

Battery 10 of the present invention is made and assembled in the following manner. Casing 12 is formed of metal, preferably 304L stainless steel, and by way of example in an illustrative battery casing 12 is 51.9 mm long between end walls 18,10, 33.3 mm high between bottom wall 22 and lid 24, and 13.5mm wide between sidewall 14,16. The anode is formed by providing the pair of ribbon-like lithium elements 62,64 and pressing them on opposite sides of the nickel screen 54. By way of example, in an illustrative battery each lithium ribbon is 7 mm thick and has a surface area per side of 13,903 square inches. The resulting illustrative ribbon anode structure has a length of 15.278 inches and a width of 0.91 inch. It is wrapped in the single layer or sheet 68 of separator material which is pressed on the anode structure and heat sealed around the edges. By way of example, in an illustrative battery separator 68 is a single layer of Pellon 2107 0.008 inch thick polypropylene non-woven separator material.

Each of the cathode plates 40 is made by first preparing a cathode mix of active material and binder and then drying the prepared mixture at a particular temperature for a short time prior to use. By way of example, in an illustrative cell, the cathode mix comprises 94 weight percent $AgV_2O_{5.5}$, three weight percent Teflon powder, two weight percent graphite powder and one weight percent carbon. This ratio of dry materials is thoroughly mixed in a ball mill and dried overnight at 140° C. for use. Each cathode plate is formed by placing half the appropriate weight of the foregoing cathode mixture in a pressing fixture, placing the cathode screen 44 on the top of the mixture, adding the remaining cathode mix, inserting the top half of the pressing fixture and applying pressure, for example 36,000–38,000 lbs. per square inch for about 45 seconds. Alternatively, the entire mixture can be placed on the screen in a manner allowing about half to pass through into the lower portion of the fixture. A silver vanadium oxide cathode for lithium cells and method of making same is described in U.S. Pat. No. 4,310,609 entitled "Metal Oxide Composite Cathode Material For High Energy Density Batteries" issued Jan. 19, 1982, the disclosure of which is hereby incorporated by reference. The method disclosed in that patent can be used to make the silver vanadium oxide used in the cathode of the present invention.

The foregoing dry pressed cathode pellet has the advantage of a relatively longer shelf life and the dry pressing method is easier to mechanize. As an alternative to the dry pressing method, a wet pressing method can be employed where one or more drops of liquid electrolyte are added to the cathode mixture prior to pressing. The electrolyte can be the same as that employed in the cell and in the foregoing illustrative example, approximately 1ml of electrolyte is added dropwise over the top of the mix after the remaining mix is added to the fixture and prior to inserting the top half of the fixture in place. The wet pressed cathode pellet is believed to enhance the performance and rate capability of the resulting battery and can be employed in manufacturing processes where the pellet is assembled in the cell relatively soon after manufacture thereof.

In the battery of FIGS. 1–12 a total of eight cathode elements or plates is employed, and the two outer or end cathode plates are slightly smaller in overall dimension to accommodate the shape of casing 12. By way of example, in an illustrative battery, the outer cathode plates have dimensions of 1.760 inch by 0.910 inch and a thickness of 0.0290 inch and a surface per side of 1.5964 square inches. Each of the remaining inner cathode plates has dimensions of 1.840 inch by 1.00 inch with a thickness of 0.0252 inch and a surface area per side of 1.8345 square inches. Each of the cathode plates contains 2.50 grams of cathode mixture. Each cathode plate is wrapped in the single layer or sheet 50 of separator material which is pressed on the cathode plate and heat sealed around the edges. By way of example, in an illustrative battery, separator 50 is a single layer of Celgard 5511 0.005 inch thick non-woven polypropylene separator material.

The battery of FIGS. 1–12 is assembled in the following manner. The anode 12 is folded into a serpentine-like subassembly as shown in FIG. 10. The cathode plates 40a–40h are inserted between the folds of the anode 42, and the resulting cell stack subassembly is inserted into casing 12 into the position shown in FIGS. 2–5 after insertion of the cell stack insulator strips 84,86 previously described. The anode leads or tabs 56,57 58 and 59 are welded to the corresponding inner surfaces of the casing sidewalls 14,16. The cell stack insulator cover 90 is positioned in place with cathode leads 46a–46h inserted through the corresponding slots 102a–102h. Then the cathode leads or tabs 46a–46h are bent or formed in the right-angle shapes as previously described and shown in FIGS. 3 and 5 and are welded together. Next, the couple 142 is secured to the end of pin 28 and intermediate lead 108 is welded at one end to cathode lead 46 as previously described. The header sub-assembly comprising lid 24, insulator and seal structure 30 fixed therein and terminal pin 28 and extending through and held in seal structure is brought into proximity with the open end of the casing 12. Then the other end of intermediate lead 108 is welded to the couple 142 on the end of pin 28 and the lid 24 is positioned or seated in place on the open end of casing 12 and then is welded in place.

Next, liquid electrolyte is introduced to casing 12 through fill opening 32 in lid 24 and in an amount sufficient to occupy at least the volume between anode 42 and cathode plates 40 and between the cell stack and the surrounding casing. The liquid electrolyte 190 is a combination of a lithium salt and an organic solvent. A preferred electrolye is a 1.2 molar solution of lithium trifluoromethane sulfonate, $LiCF_3SO_3$, in 50:50 volume:volume propylene carbonate dimethoxyethane. The liquid electrolyte is introduced through fill opening 32 including the passage in ferrule 144 by a delivery tube or other suitable means and flows through opening 104 in cover 90 into the region of the cell stack. When filling is completed, the first plug or sphere 168 is inserted in ferrule 144 and the second plug or cap 170 is inserted in opening 32 and close welded in place. The resulting battery is in a case negative electrical configuration, i.e. the anode 42 is electrically connected to the conductive casing 12 serving as the negative polarity external electrical connection for the battery and pin 28 is connected to the cathodes serving as the positive external electrical connection for the battery.

Figure 13:
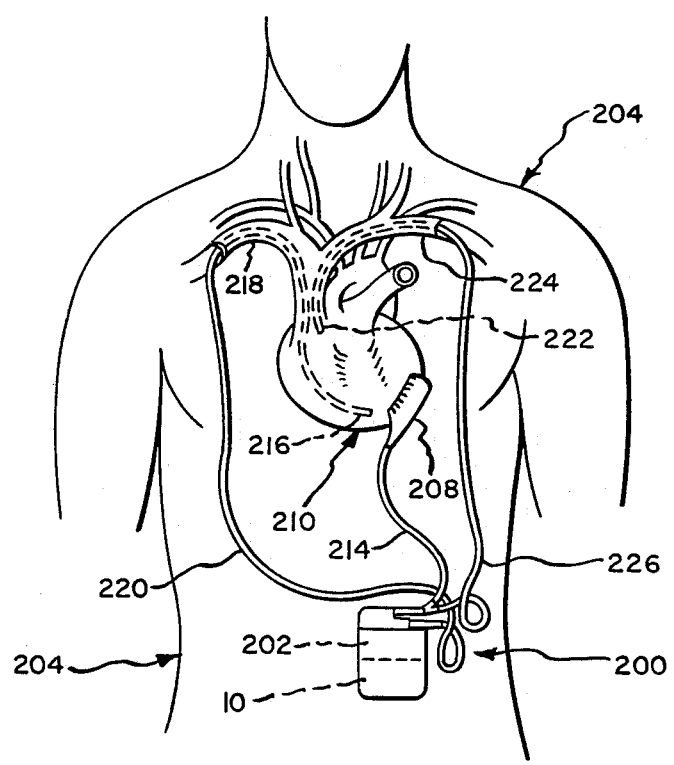
FIG. 13 is a diagrammatic view illustrating one use of the battery of FIG. 1 with an implanted cardiac defibrillator.

An important and advantageous use of battery 10 of the present invention is with an implantable cardiac defibrillator. As shown in FIG. 13 an implantable cardiac defibrillator generally designated 200 including a pulse generator 202 and battery 10 of the present invention is implanted in the abdominal area of a patient 204. The case 12 and terminal 28 of battery 10 are electrically connected to inputs of pulse generator 202 in a known manner. The defibrillator 200 is enclosed in a housing of human body reaction free material. A defibrillating apical patch electrode 208 is placed surgically in contact with external tissue of the heart 210 of the patient 204. Electrode 208 is connected electrically by a condutor 214 to pulse generator 200, the conductor 214 being enclosed in human body reaction free material. A bipolar endocardial electrode 216 is positioned in the heart 210 through the right subclavian vein 218 and is connected electrically by a conductor 220 to pulse generator 202. A superior vena clava electrode 222 is positioned in the heart 210 through the left subclavian vein 224 and is electrically connected by conductor 226 to pulse generator 202. Both conductors 220,226 are enclosed in sheaths of human body reaction free material. For a more detailed discussion of implantable cardiac defibrillators, reference may be made to any of the following: "The Implantable Automatic Cardioverter Defibrillator", Edward A. Platia, *Applied Cardiology*, September/October, 1984, page 10–13, "The Implantable Cardio-verter Defibrillator; An Update", M. Mirowski, *The Journal of Cardiovascular Medicine*, March 1984, Vol. 9, No. 3, pages 191–199and "The Implantable Defibrillator In Ventricular Arrhythmias", Winkle, *Hospital Practice*, March, 1983, Vo. 18, No. 3, page 149–165, the disclosure of each of which is hereby incorporated by reference.

Battery 10 of the present invention operates in the following manner. When the ionic conductive electrolytic solution becomes operatively associated with the anode and cathode of the cell, an electrical potential differnce is developed between terminals operatively connected to the anode and cathode. The electrochemical reaction at the anode includes oxidation to form metal ions during discharge of the cell. The electrochemical reaction at the cathode involves conversion of ions which migrate from the anode to the cathode into atomic or molecular forms. The large surface area provided by the stacked arrangement of anode and cathode sections provides high current capability.

Battery 10 of the present invention advantageously delivers high capacity, shows good current pulse behavior at various levels of discharge and has a sloping discharge curve. In particular, battery 10 according to the foregoing example and for use in defibrillator applications can deliver 10 second, 2.0 ampere pulses with 5.5 ampere hour capacity. The cathode active material comprising silver vanadium oxide advantageously has high volumetric capacity and high rate capability. For example, $AgV_2O_{5.5}$ is 1.4 times greater than $V_2O_5$ in volumetric capacity. In addition, $AgV_2O_{5.5}$ is a semiconductor which allows cathodes to be fabricated with less conductive material, i.e. carbon, to be added thereby resulting in higher volumetric capacity electrodes. Another advantage of silver vanadium oxide is that it provides a sloping discharge curve in a lithium cell. A $Li/AgV_2O_{5.5}$ cell has a sloping open circuit voltage curve as a function of depth of discharge from 3.2 volts beginning of life to 2.0 volts end of life. This allows the state of charge or expended battery capacity to be monitored and end of life of the battery to be predicted. This obviously is advantageous in an implanted device such as a defibrillator. The liquid organic electrolyte, i.e. 1.0 or 1.2M $LiCF_3SO_3$ or 1.0M $LiAsF_6$ in 50:50 PC:DME advantageously offers high rate capability yet has not been found to present a hazard problem such as venting or explosion on internal or external short circuit. With respect to the insulator and seal structure 30, corrosion resistant glass/pin combinations such as Ta23 glass with molybenum pin fed through has superior corrosion resistance advantageously resulting in longer cell life. In particular, the combination of molyblenum pin and Ta23 glass advantageously provides resistance to internal cell materials, the role of the glass being augmented by provision of the elastomer 134 which retards lithium ions. The individual wrapping or encapsulation of anode 42 and the individual cathode plates 40 advantageously provides an enhanced reliability of the cell. In particular, in the event that any one separator should happen to fail, separators are provided on all the other anode and cathode components.

An illustrative cell according to the example previously described has a theoretical capacity of 5.5 ampere hours, calculated D.C. resistance of 0.15 ohm–0.35 ohm, internal impedance at 1 KHZ of 0.30 ohm–0.50 ohm, and open circuit voltage of 3.2 volts at beginning of life and 2.0 volts at end of life. The cell has an energy of 8 watt hours calculated to a 2.0 volt cutoff under a 2.0 ampere pulse load, the pulse load regime being a train of five 10 second 2 ampere pulses with 10 second open circuit rests between pulses. The illustrative cell has a weight of about 64 grams and a volume of about 24 cubic centimeters. The gravimetric energy density is 0.1 watt-hour/gram and the volumetric energy density is 0.221 watt hours/cubic centimeters. The foregoing is illustrated further by FIG. 28 which is a graph of open circuit and voltage under pulse vs. capacity where curve 230 is open circuit voltage and curve 232 is voltage under 2 ampere pulse load.

The cathode advantageously includes as active material $Ag_xV_2O_y$ where x is in the range from about 0.5 to about 2.0 and y is in the range from about 4.5 to about 6.0. The various advantages of silver vanadium oxide as cathode active material in the cell of the present invention are set forth hereinabove. For an additional discussion of this material and its advantages, reference may be made to "Effect of Silver Content On the Performance Of Primary Lithium/Silver Vanadium Oxide Batteries", E. S. Takeuchi and P. Keister, Electrochemical Society, Oct. 13–18, 1985, Las Vegas, Nevada, Abstract No. 125, the disclosure of which is hereby incorporated by reference. The cathode mixture also may contain lithium salts, solid lithium ion conducting electrolyte and/or surfactant. In addition, advantage can be taken of the various structural attributes of the cell of the present invention including the folded anode and individually wrapped cathode plates while using as alternative cathode active materials $V_2O_5$, $MnO_2$ or $CF_x$ where x is approximately 1.

As previously described, the liquid or organic electrolyte is a combination of a lithium salt and an organic solvent. For the electrolyte combination, the lithium salt can include either alone or in combination $LiCF_3SO_3$, $LiBF_4$, $LiClO_4$, $LiAsF_6$, $LiPF_6$ and $LiO_2$, and the solvent can include propylene carbonate, dimethoxyethane, gamma-butyrolactone, two-methyl-tetrahydrofuran, dimethyl sulfite, and methyl formate. Salt concentration typically is 1.0 or 1.2 molar and solvent mixtures are typically 50:50 volume:volume PC:DME.

The case negative battery design of FIGS. 2–12 is considered to have the advantage of better long term performance including lower self discharge, higher temperature stability and minimal corrosion of elements in the cell as a result of suitable selection of material for the cathode current collector. As an alternative, the battery of the present invention can be in a case positive electrical configuration which now will be described.

Figure 17:
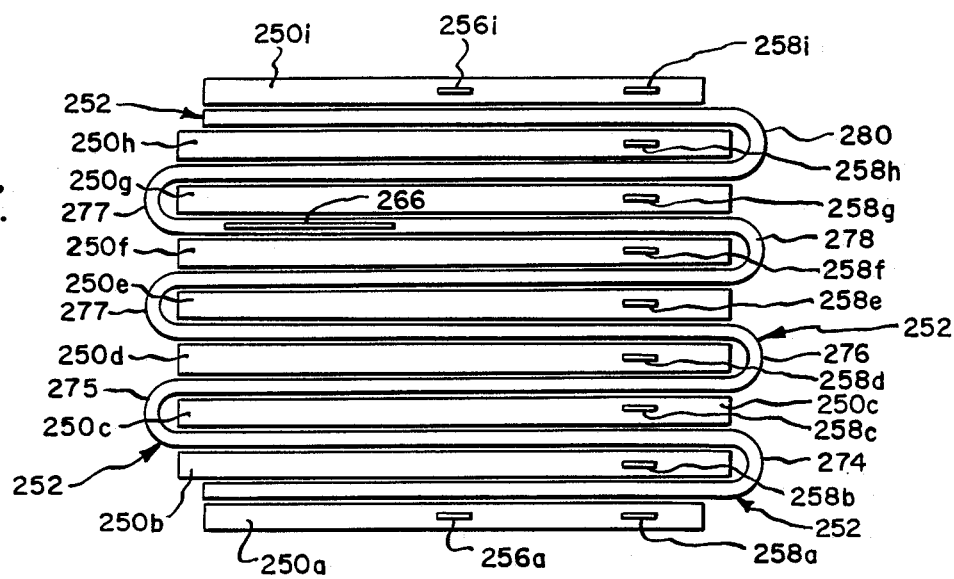
FIG. 17 is a top plan view of the cell stack assembly of the battery of FIG. 14.
Figure 18:
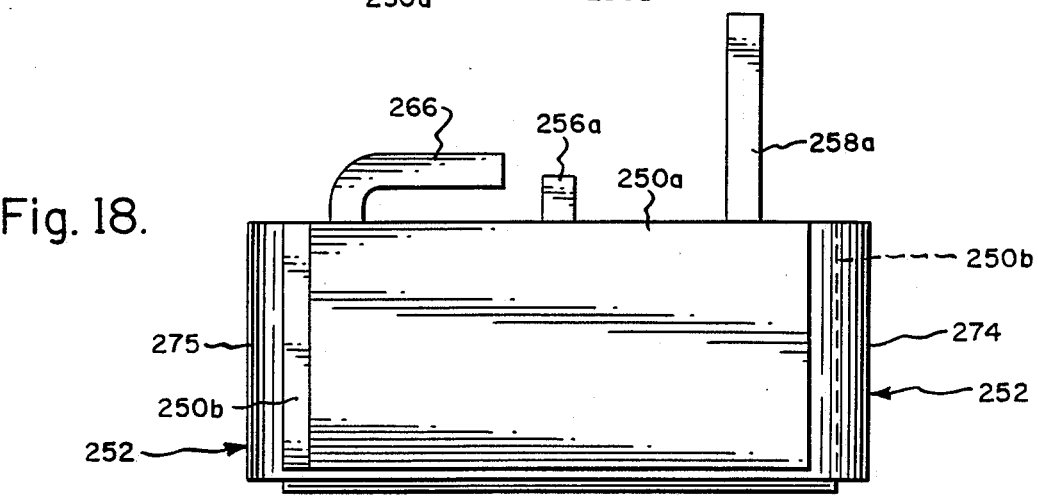
FIG. 18 is a side elevational view of the assembly of FIG. 17.

FIGS. 14–22 illustrate a battery 240 according to the present invention in a case positive electrical configuration. Components of battery 240 which are identical to those of battery 10 in FIGS. 1–12 are identified by the same reference numeral but with a prime designation. Briefly, in battery 240 a single lead from the anode is connected electrically to pin 28' extending through insulator and seal structure 30', and a plurality of cathode leads are connected electrically to casing 12' of electrically conductive material. Referring now in detail to the drawings, casing 12', lid 24' pin 28' insulator and seal structure 30' and cap structure 34' are substantially the same as corresponding components in the battery of FIGS. 1–12. Battery 240 includes cathode means 250 comprising a plurality of components or plates in spaced apart relation and lithium anode means 252 comprising a plurality of anode sections interposed between the cathode plates. There are nine cathode plates 250a, 250b, 250c, 250d, 250e, 250f, 250g, 250h and 250i arranged in casing 12' in spaced apart, stacked relation and disposed substantially parallel to each other and to the sidewalls 14',16' of casing 12'. The cathode plates 250 are generally rectangular in overall shape and of a size extending along substantially the entire dimension of casing 12' between ends 18',20' and extending along a major portion of the distance between bottom 22' and lid 24'. As shown in FIGS. 14, 17 and 18 the outermost cathode plates 250a and 250i in the stack are slightly shorter in length and width than the remainder of the cathode plates 250b–250h to accommodate the curvature of casing 12'. The cathode plates 250 of battery 240 contain the same cathode active material as cathode plates 40 of battery 10.

FIG. 20 shows in further detail one of the two cathode components or plates, for example plate 250a it being understood that cathode plate 250i is identical. Cathode 250a comprises a cathode conductor including a body portion 254a and a pair of spaced apart lead portions 256a and 258a extending from the same side of body portion 254a. Leads 256a, 258a extend at right angles to the side of body portion 254a and parallel to each other. Lead 256a is relatively shorter in length and is located substantially midway between the ends of body portion 254a, and the longer lead 258a is located near one end of body portion 254a. The conductor body portion 254a is in the form of a thin sheet of metal screen, for example stainless steel, and each lead portion 256a,258a is in the form of a solid thin tab. Cathode 250a further comprises a body 260a of cathode mixture including cathode active material and binder. The cathode active material binder and optional additives are the same as those employed in the embodiment of FIGS. 1–12 and the method of making the cathode including pressing to form a pellet likewise is the same. The resulting pellet is enclosed or encapsulated in an envelope 262a of separator material, for example polypropylene or polyethylene, in a manner similar to that employed in the cell of FIGS. 1–12.

FIG. 21 shows in further detail one of the seven inner cathode components or plates, for example plate 250b, it being understood that plates 250c–250h are identical. Cathode 250b comprises a cathode conductor including a body portion 254b and a single lead portion 258b. The conductor portion 254b is in the form of a thin sheet of metal screen, for example titanium or stainless steel, and lead portion 258b is in the form of a solid thin tab extending from one side of screen 254b. Lead portion 258b is at the same location and is of the same size as lead 258a of cathode 250a, so that when cathodes 250a,250b are arranged in stacked relation, leads 258a,258b are in registry. The same is true for the remaining cathode plates. Cathode 250b further comprises a body 260b of cathode mixture including cathode active material binder and possibly some additives which are the same as those employed in cathode body 260a. The method of making cathode 250b including pressing to form a pellet likewise is the same. The resulting pellet is enclosed or encapsulated in an envelope 262b of separator material, for example polypropylene or polyethylene, in a manner similar to that used for cathode 250a.

Figure 19:
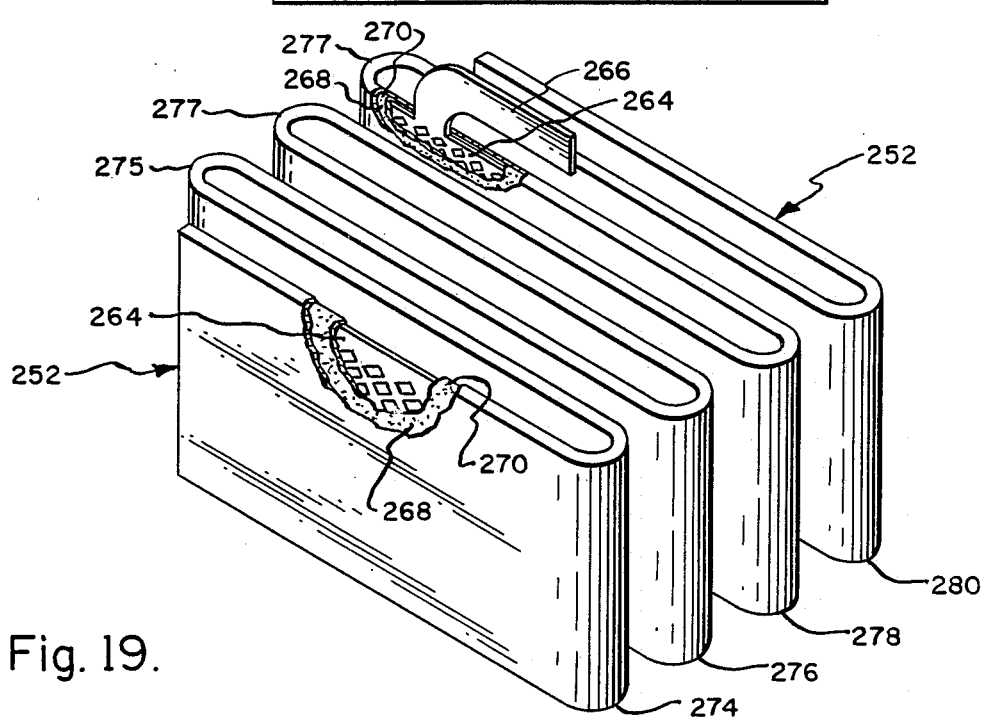
FIG. 19 is a perspective view with parts removed of the anode of the battery of FIG. 14.

The anode means 252 comprises a continuous elongated element or structure of alkali metal, preferably lithium or lithium alloy, enclosed within separator material and folded into a plurality of sections which are interposed between the cathode plates 250a–250i. As shown, for example, in FIGS. 17 and 18, anode means 252 is folded in a manner such that the sections thereof extend along both opposite sides of each of the inner cathode plates 250b–250h and along the inner sides of the outer cathode plates 250a and 250i. Referring now in detail to FIG. 19, anode means 252 comprises an elongated continuous ribbon-like anode conductor element 264 in the form of a thin metal screen, for example nickel alloy. Conductor 264 includes a terminal or contact tab 266 extending therefrom, in particular from one edge and located offset from the center of the folded arrangement and inwardly from one side thereof. Anode means 252 further comprises a pair of elongated ribbon-like lithium elements 268 and 270 pressed together against opposite sides of conductor element 264 to form an anode structure. The lithium elements 268,270 are substantially equal in width and length to conductor element 264. The resulting anode structure is a sandwich-like construction with conductor 264 between the lithium elements 268,270. Anode means 252 further comprises separator material 272 encapsulating the anode structure. In particular, the anode structure comprising conductor 264 and lithium plates 268,270 is enclosed or wrapped in an envelope of separator material, for example polypropylene or polyethylene. Thus, with the exception of the single lead 266 and its location anode 252 is substantially similar to anode 242 in the battery of FIGS. 1–12.

The resulting anode structure is folded at spaced intervals along the length thereof to form a serpentine-like structure as shown in FIG. 19 to receive cathode plates between the folds thereof. In particular, the anode means is folded at the intervals 274,275,276,277,278,279 and 280. Cathode plate 250b is received between the folds or leaves in anode 252 defined about interval 274 as shown in FIGS. 17 and 18. Cathode plate 250c is received between the folds about interval 275. Similarly, the remaining cathode plates 250d–250h are received between the folds defined about the intervals 276,280, respectively.

The folded anode structure 252 with cathode plates 205a–250i comprises a cell stack sub-assembly which is received in casing 12'. The opposite outer surfaces of cathode plates 250a and 250are located adjacent the inner surfaces of casing sidewalls 14',16' as shown in FIG. 16. As in the embodiment of FIGS. 1–12, the cell stack occupies a major portion of the internal volume of casing 12'. First and second cell stack insulators 84' and 86' are provided in a similar manner and for the same purpose as insulators 84,86 in FIGS. 1–12. As an alternative, a single container or bag of insulating material holding the cell stack assembly can be employed.

A cell stack insulating cover 290 is located in casing 12' adjacent the upper surface of the cell stack and in spaced relation to lid 24' as viewed in FIGS. 14 and 16. Cover 290 shown in further detail in FIG. 22 has a planar body portion 292 including parallel side edges 294,295, parallel end edges 296,297 and curved or rounded corners so as to conform closely to the configuration defined by the inner surfaces of the sidewalls 14',16', and endwalls 18',20'. Cover 290 is provided with a pair of flanges or tabs 298,300 extending from side edges 294 and 295 and disposed at about right angles to body 292. Tabs 298 and 300 are used to insulate the cathode leads from the inner surfaces of casing sidewalls 14',16'. Body 292 is provided with a plurality of spaced-apart, longitudinally disposed slots 302b–302h which are arranged in a row extending transversely across body 292 and located near the end of the body away from tabs 298,300. Slots 302b–302h are of a size, configuration and location to receive tabs 258b–258h, respectively, extending from the cathode pellets 250b–250h, respectively. Thus, the cathode leads or tabs 258a–258i extend from cathode plates or pellets 250a–250i in the stack below cover 290, and leads 258b–258h extend through the slots 302b–302h into the open region between cover 290 and lid 24'. Leads 258a and 258i extend up along edges 294 and 295, respectively, of cover 290. Cover body 292 also is provided with a single longitudinally extending slot 304 generally between tabs 298,300 at a location and of a size to receive anode lead or tabe 266 extending therethrough. Also, cover body 292 is provided with a generally circular opening 306 generally centrally thereof for the same purpose as opening 104 in cover 90 of FIG. 12.

Each of the cathode leads 258c–258i is bent or formed into approximately a right angle as shown in FIG. 16 with the legs thereof extending in the same direction and with the lower surface of one leg contacting and secured such as by welding to the upper surface of the neighboring leg. Lead 258b is bent into a formation including a right angle portion like the other leads and then the outer leg is formed into a return bend. Lead 258a is of considerably greater length from the other leads and is bent into a right angle extending in the opposite direction and overlying the remaining tabs 258b,258i as shown in FIG. 18. Lead 258a is connected to lead 258b as shown. The remaining end portion of lead 258a extends transversely and terminates in an upwardly extending formation or tab 310 which is welded to the inner surface of casing wall 16'. Leads 256a and 256i are welded to the inner surface of casing wall 14' and 16', respectively. Anode lead 266 extends through the slot 304 and is bent to extend longitudinally toward end wall 16' whereupon it is welded to the couple 142' associated with pin 28'.

The battery 240 of FIGS. 14–22 is assembled in the following manner. The anode 252 is folded into a serpentine-like subassembly as shown in FIG. 19. The inner cathode plates 250b–250h are inserted between the folds of the anode and the outer cathode plates 240a,2-40i are placed against the outer surfaces of the anode arrangement. Then the resulting cell stack subassembly is inserted into casing 12' into the position shown in FIG. 16 after insertion of the cell stack insulator strips previously described. The cathode leads or tabs 256a,2-56i are welded to the corresponding inner surfaces of the casing sidewalls 14',16'. The cell stack insulating cover 290 is positioned in place with cathode leads 258b–258h inserted through the corresponding slots 302b–302h and anode lead 266 inserted through slot 304. Then the cathode leads or tabs 258a–258i are bent or formed in the right angle shapes as previously described and shown in FIG. 16 and are welded together. The formation or tab 310 is welded to the inner surface of casing wall 16'. Then anode lead 266 is bent or formed to the condition shown in FIGS. 14 and 15. The header subassembly comprising lid 24', insulator and seal structure 30' fixed therein and terminal pin 28' extending through and held in seal structure 30' is brought into proximity with the open end of the casing 12'. Then the free end portion of anode lead 266 is welded to the couple 142' on pin 28' and the lid 24' is positioned or seated in place on the open end of casing 12' and then is welded in place.

Next, liquid electrolyte is introduced to casing 12' through fill opening 32' in lid 24' and in an amount sufficient to occupy at least the volume between anode 252 and cathode plate 250 and between the cell stack and the surrounding casing. The liquid electrolyte 190' can be the same as those suitable for the cell 10 of FIGS. 1–12. The liquid electrolyte is introduced through fill opening 32' including the passage in ferrule 144' and flows through opening 306 in cover 290 into the region of the cell stack in a manner similar to that of cell 10'. When filling is completed, the first plug or sphere is inserted in ferrule 144' and the second plug or cap is inserted in opening 32' and close welded in place. The resulting battery is in a case positive electrical configuration, i.e. the cathodes 250 are electrically connected to the conductive casing 12' serving as the positive polarity external electrical connection for the battery and pin 28' is connected to the anode 252 serving as the negative external electrical connection for the battery.

Battery 240 likewise finds advantageous use as a power source for an implantable cardiac defibrillator. It advantageously delivers high capacity, shows good pulsing behavior at various levels of discharge and has a sloping discharge curve similar to battery 10' of FIGS. 1–12. Battery 240 utilizes all the advantages of cathode active material including silver vanadium oxide previously described. It also includes the benefits of the Ta23 glass seal of structure 30' and the molybendum pin 28' together with individual wrapping and encapsulation of anode 252 and the individual cathode plates 250 as previously described. The cathode mixture in battery 240 also may contain lithium salts, solid lithium ion conducting electrolyte and/or surfactant. In addition, as in the cell of FIG. 1–12, advantage can be taken of the various structural attributes of the cell of the present invention including the folded anode and individually wrapped anode and cathode plates while using as alternative cathode active material $V_2O_5$, $MnO_2$ or $CF_x$ where x is approximately one.

FIGS. 23–27 show an alternative form of cathode and cell stack arrangement according to the present invention. Briefly, the cathode is a single or integral structure including a one piece screen having individual segments and cathode active material sections or pellets associated with the segments to form a chain-like structure which is enclosed or encapsulated in separator material. The anode is similar to that shown in FIG. 10. Starting from a flat condition of both anode and cathode they are folded in a manner weaving them into a cell stack arrangement. Referring now in detail to FIG. 23, the cathode 310 comprises a cathode conductor including a plurality of segments or portions, in the present illustration nine segments 312a–312i. Each segment is joined to the neighboring segment by a pair of spaced apart leads or tabs 314,316 extending from one side edge of the segment and meeting the second side edge of the neighboring segment. For example, tabs 314a, 316a extend from segment 312a and join it to segment 312b. Thus the cathode conductor comprises a plurality of individual sections joined in end-to-end relation. The tabs 314i,316i extending from segment 312i are retained for a purpose which will be described. Segment 312a is provided with a pair of additional spaced apart leads or tabs 318,320 of relatively greater length and extending in spaced apart relation from the side of segment 312 opposite that from which leads 314a,316a extend. The elongated cathode conductor including the segments and tabs can be photoetched or otherwise formed from a continuous thin sheet of metal screen. Alternatively individual segments and associated tabs can be provided and then connected together such as by spot welding.

Cathode 310 further comprises a plurality of sections or pellets of cathode mixture including cathode active material and binder, each section or pellet of cathode active material being associated with a corresponding one of the cathode conductor segments. Thus, cathode 310 comprises the sections or pellets 320a–320i formed on the corresponding cathode conductor sections 312a–312i. The cathode active material and binder and optional additives are the same as those employed in the embodiments of FIGS. 1–22, and the method of making the cathode including pressing to form a pellet likewise is the same. The resulting cathode structure as shown in FIG. 23 is chain-like, with the individual cathode conductor segments and associated cathode sections or pellets linked together by the intervening tabs or leads.

The chain-like cathode structure of FIG. 23 is enclosed or encapsulated in an envelope 324 of separator material, for example, polypropylene or polyethylene, as shown in FIG. 24 and in a manner similar to that employed in the cells of FIGS. 1–22. The anode generally designated 326 in FIG. 24 is similar to anode 252 shown in FIG. 19. Anode 326 is illustrated in FIG. 24 in flat, extended condition and includes an elongated continuous ribbon-like conductor element in the form of a thin metal screen, for example nickel, sandwiched between a pair of ribbon-like lithium elements which are pressed together against opposite sides of the conductor to form an anode structure. A single terminal or contact tab 328 extends therefrom in a manner similar to tab 266 of anode 252 in FIG. 19. The anode structure comprising the conductor and lithium plates is enclosed or wrapped in an envelope of separator material, for example, polypropylene or polyethylene, in a manner similar to anode 252 of FIG. 19.

The cathode 310 and anode 326 are placed flat and in endwise overlapping condition and at right angles to each other as shown in FIG. 24. They are alternately folded over one another to form the resulting interwoven cell stack subassembly shown in FIGS. 25-27. As shown in FIG. 26, after the assembly is formed by the foregoing folding operation, leads 318, 320 are folded to the condition shown in FIGS. 25-27 extending along the side surface of the assembly. Alternatively, the anode and cathode can be placed flat, in overlapping and coincident relation with the ends in spaced relation and then folded together to form a cell stack subassembly. The assembly is placed in a cell casing in a manner similar to the battery of FIGS. 14-22 and the leads or tabs 314i, 316i, 318 and 320 are welded to corresponding inner sidewall surfaces of the conductive cell casing. A cell stack insulating cover 330 is employed similar to cover 290 shown in FIG. 22 without the slots 302b-302i. For convenience, cover 330 is shown only in FIG. 26. The anode lead 328 is welded to the terminal pin similar to that of the battery of FIGS. 14-22. The resulting cell is in a case positive electrical condition like the cell of FIGS. 14-22. The same liquid electrolyte is employed as in the previous embodiments and the cell is sealed in the same manner. The resulting cell also finds advantageous use as a power source as an implantable cardiac defibrillator with the same advantages as the cells of FIGS. 1-22.

The cell of the present invention can include other anode and cathode structures and arrangements without departing from the spirit and scope of the invention. For example, the anode can comprise a series of plates, each comprising an anode conductor sandwiched between a pair of lithium plates and enclosed within separator material heat sealed around the edges. With such an anode the cathode can comprise a series of plates as in the embodiments of FIGS. 1-22 interposed between the anode plates to form a cell stack assembly. Alternatively, the cathode can comprise a continous elongated structure folded in serpentine fashion with the anode plates interposed between the folds or leaves of the cathode to form a cell stack assembly. Such continuous cathode would comprise an elongated conductor similar to that shown in FIG. 23 but continuous without interconnecting tabs, cathode material pressed onto the conductor to form an elongated continuous body and an outer covering or envelope of separtor material. As a further alternative, with such a continuous cathode a continuous anode similar to that shown in FIGS. 10, 19 and 24 can be employed. The cathode and anode would be folded or interwoven together in a manner similar to that described in connection with FIGS. 23-27 to form a cell stack assembly. As an alternative to the case positive and case negative configuration described herein, the battery of the present invention can have a case neutral configuration. That would include another pin and insulated seal structure extending through the lid similar to pin 28 and seal 30. The anode and cathode each would be connected electrically to a corresponding one of the pins.

It is therefore apparent that the present invention accomplishes its intended objects. There is provided a new and improved solid cathode, liquid organic electrolyte lithium battery for delivering high current pulses having the ability to deliver a current pulse and rapidly recover its open circuit voltage and having high capacity, low-self discharge and good pulsing behavior at all levels. The battery has the requisite safety in operation and proper size and configuration suitable for implantation, and the cell chemistry includes a reliable indication of the depth of discharge or approaching end-of-life during operation. The cell of the present invention is economical to manufacture and effecient and effective in operation. While several embodiments have been described in detail, that is for the purpose of illustration, not limitation.

I claim:

1. A method of making an anode-cathode assembly for a solid cathode non-aqueous liquid electrolyte alkali metal cell for delivering high current pulses comprising the steps of:
   (a) providing a cathode mix comprising cathode active material;
   (b) providing a cathode conductor comprising a body portion and a lead portion;
   (c) pressing said cathode mix on said conductor body portion to form a pellet;
   (d) encapsulating said pellet with separator material;
   (e) providing a plurality of cathode elements according to the foregoing steps;
   (f) providing an elongated alkali metal anode comprising an elongated ribbon-like anode conductor, a pair of elongated ribbon-like alkali metal elements pressed together against opposite sides of said conductor to form an anode structure and separator material encapsulating said anode structure; and
   (g) folding said anode along the length thereof to form a serpentine structure; and
   (h) placing said plurality of cathode elements between corresponding ones of the folds of said serpentine anode structure.

2. A method according to claim 1, wherein said step of providing a cathode mix is followed by drop-wise addition of a quantity of said electrolyte to said mix prior to said step of pressing.

3. A method according to claim 1, further including the step of heat treating said pellet after said step of pressing.

4. A method of making an anode-cathode assembly for a solid non-aqueous liquid electrolyte alkali metal cell for delivering high current pulses comprising the steps of:
   (a) providing an elongated ribbon-like anode conductor element;
   (b) providing a pair of elongated ribbon-like alkali metal elements;
   (c) pressing said alkali metal elements against said conductor element to form an elongated ribbon-like anode structure;
   (d) encapsulating said anode structure with separator material;
   (d) folding said anode structure at spaced intervals along the length thereof to form a serpentine structure;
   (f) providing a plurality of separate cathode elements; and
   (g) placing said plurality of cathode elements between corresponding ones of the folds of said serpentine anode structure.

5. A method according to claim 4 wherein said alkali metal elements are of lithium.

6. A method of making an anode-cathode assembly for a solid cathode non-aqueous liquid electrolyte alkali metal cell for delivering high current pulses comprising the steps of:
- (a) providing a cathode conductor comprising a plurality of individual sections joined in end-to-end relation;
- (b) providing a cathode mix comprising cathode active material and binder;
- (c) pressing said cathode mix on said conductor sections to provide a corresponding plurality of individual pellets;
- (d) encapsulating said pellets with separator material;
- (e) providing an elongated alkali metal anode comprising an elongated ribbon-like anode conductor, a pair of elongated ribbon-like alkali metal elements pressed together against opposite sides of said conductor to form an anode structure and separator material encapsulating said anode structure; and
- (f) placing said cathode and anode in flat and in overlapping condition and folding said anode and cathode one over the other to form an anode-cathode assembly.

7. A method of making an anode-cathode assembly for a solid cathode non-aqueous liquid electrolyte alkali metal cell comprising the steps of:
- (a) providing an elongated cathode comprising a cathode conductor comprising a plurality of individual sections joined in end-to-end relation, a corresponding plurality of individual pellets of cathode active material pressed onto said conductor section and separator material encapsulating said pellets;
- (b) providing an elongated alkali metal anode comprising an elongated ribbon-like anode conductor, a pair of elongated ribbon-like alkali metal elements pressed together against opposite sides of said conductor to form an anode structure and separator material encapsulating said anode structure; and
- (c) placing said cathode and anode in flat and in overlapping condition and folding said anode and cathode one over the other to form an anode-cathode assembly.

8. A method according to claim 7, wherein said cathode and anode are placed endwise in said overlapping condition and at right angles ot each other and then folded alternately one over the other to form an interwoven anode-cathode assembly.

9. A method according to claim 6, wherein said cathode and anode are placed coincident in said overlapping condition with the ends thereof in spaced relation prior to folding.

* * * * *